United States Patent [19]

Stoffel et al.

[11] 4,088,472

[45] May 9, 1978

[54] AGRICULTURAL PROCEDURE

[75] Inventors: Paul J. Stoffel, St. Louis; Ignatius Schumacher, Webster Groves, both of Mo.

[73] Assignee: Monsanto Company, St. Louis, Mo.

[21] Appl. No.: 513,577

[22] Filed: Dec. 13, 1965

[51] Int. Cl.² .............................................. A01N 9/22
[52] U.S. Cl. ..................................................... 71/92
[58] Field of Search ................... 260/307.2; 71/2.5, 92

[56] References Cited

U.S. PATENT DOCUMENTS

| | | | |
|---|---|---|---|
| 2,895,817 | 7/1959 | Luckenbaugh | 71/92 |
| 2,985,663 | 5/1961 | Carmack et al. | 260/309.7 |
| 3,133,079 | 5/1964 | Luckenbaugh | 260/309.6 |
| 3,201,410 | 8/1965 | Morel et al. | 260/307 |
| 3,254,984 | 6/1966 | Johnson | 71/99 |

FOREIGN PATENT DOCUMENTS

| | | | |
|---|---|---|---|
| 615,858 | 3/1961 | Canada | 71/2.5 |
| 1,394,774 | 3/1965 | France | 71/92 |
| 1,039,302 | 9/1958 | Germany | 71/2.5 |
| 910,022 | 11/1962 | United Kingdom | 71/2.5 |

OTHER PUBLICATIONS

Zinner I, Arch. Pharm. 294, 765-769 (1961).

Zinner et al. I, II, Arch. Pharm. 298, 580-587, 805-809 (1965).

Primary Examiner—Glennon H. Hollrah
Attorney, Agent, or Firm—Arnold H. Cole

[57] ABSTRACT

The growth of vegetation is controlled by subjecting the vegetation to the phytotoxic effects of a compound of the formula

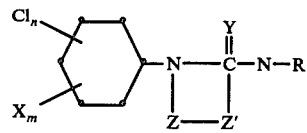

wherein Y is selected from the class consisting of oxygen and sulfur; wherein Z and Z' are each selected from the class consisting of oxo ($>C=O$) and oxy ($—O—$), provided that Z and Z' are different; wherein R is alkyl of not more than four carbon atoms; wherein X is selected from the class consisting of alkyl of not more than four carbon atoms, alkoxy of not more than four carbon atoms and nitro; wherein $n$ is an integer from zero to three; and wherein $m$ is an integer from zero to one.

12 Claims, No Drawings

AGRICULTURAL PROCEDURE

This invention relates to the inhibition of undesired vegetation in agricultural soils by subjecting the said vegetation to the phytotoxic effects of certain of the oxadiazolidines as described hereinafter. More specifically, the control of vegetation growth is accomplished either by contacting the vegetation with the active compound or by applying the said compound to the soil and effecting the control pre-emergently.

The useful compounds for practicing this invention have the following generic formula:

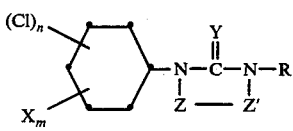

wherein Y is selected from the class consisting of oxygen and sulfur; wherein Z and Z' are each selected from the class consisting of oxo (>C=O) and oxy (—O—), provided that the Z and Z' groups are different; wherein R is alkyl having up to four carbon atoms; wherein X is selected from the class consisting of alkyl having up to four carbon atoms, alkoxy having up to four carbon atoms and nitro; wherein $n$ is an integer from zero to three; and wherein $m$ is an integer from zero to one.

The useful compounds are prepared by the reaction of an isocyanate with a hydroxyl amine and ethylchloroformate. Preparation of these compounds is described in detail by Zinner and Webber, Arch. Pharm. 298, 805–809, November 1965.

A preferred type of each of these useful compounds are those in which the benzene ring is substituted with one or more chlorine atoms.

The relative value of the oxadiazolidines of the present invention was determined by planting in greenhouse flats seeds of sixteen different plants. The planted flats were covered with ⅜ inches of additional soil and treated with the various compounds at a rate equivalent to one pound per acre. The flats were then placed on a flooded greenhouse bench and permitted to stand for 14 days. In the following tables of phytotoxic evaluation data, these plants are represented by letters as follows:

| A Morning Glory | I Foxtail |
| --- | --- |
| B Wild Oat | J Barnyard Grass |
| C Brome Grass | K Crab Grass |
| D Rye Grass | L Pigweed |
| E Radish | M Soybean |
| F Sugar Beet | N Wild Buckwheat |
| G Cotton | O Sorghum |
| H Corn | P Rice |

The relative value of each compound with respect to its phytotoxic effect on the various plants is indicated by a number as follows:

0 — no phytotoxicity
1 — slight phytotoxicity
2 — moderate phytotoxicity
3 — severe phytotoxicity
4 — dead The compounds used in the evaluation are identified in the tables below by number symbols:

(I) 2-methyl-4-(4'-ethoxyphenyl)-3,5-dioxo-1,2,4-oxadiazolidine
(II) 2-methyl-4-(4'-chlorophenyl)-3-thiono-5-oxo-1,2,4-oxadiazolidine
(III) 2-methyl-4-(4'-chlorophenyl)-3,5-dioxo-1,2,4-oxadiazolidine
(IV) 2-methyl-4-(3',4'-dichlorophenyl)-3,5-dioxo-1,2,4-oxadiazolidine
(V) 2-methyl-4-(3'-chlorophenyl)-3,5-dioxo-1,2,4-oxadiazolidine
(VI) 2-methyl-4-(4'-methylphenyl)-3,5-dioxo-1,2,4-oxadiazlidine -oxadiazolidine
(VII) 2-methyl-4-(3'-methylphenyl)-3,5-dioxo-1,2,4-oxadiazolidine
(VIII) 4-methyl-2-phenyl-5-oxo-3-thiono-1,2,4-oxadiazolidine
(IX) 2-methyl-4-(3',4'-dichlorophenyl)-3-thiono-5-oxo-1,2,4-oxadiazolidine
(X) 4-methyl-2-phenyl-3,5-dioxo-1,2,4-oxadiazolidine Table I shows the pre-emergent phytotoxic effects when the oxadiazolidines were applied to the soil of planted flats at the one pound per acre rate.

Table I

| Compound | A | B | C | D | E | F | G | H | I | J | K | L | M | N | O | P |
| --- | --- | --- | --- | --- | --- | --- | --- | --- | --- | --- | --- | --- | --- | --- | --- | --- |
| I | 0 | 0 | 0 | 0 | 1 | 3 | 0 | 0 | 1 | 0 | 1 | 2 | 0 | 2 | 0 | 0 |
| II | 0 | 1 | 1 | 3 | 0 | 3 | 0 | 2 | 3 | 3 | 3 | 3 | 0 | 3 | 3 | 1 |
| III | 0 | 0 | 0 | 1 | 0 | 1 | 0 | 0 | 3 | 0 | 3 | 3 | 0 | 2 | 1 | 0 |
| IV | 3 | 3 | 1 | 3 | 3 | 3 | 0 | 0 | 3 | 3 | 3 | 3 | 0 | 2 | 1 | 1 |
| V | 2 | 0 | 0 | 0 | 1 | 3 | 0 | 0 | 3 | 1 | 3 | 3 | 0 | 0 | 1 | 0 |
| VI | 0 | 0 | 0 | 0 | 0 | 0 | 0 | 0 | 1 | 0 | 0 | 2 | 0 | 0 | 0 | 0 |
| VII | 0 | 0 | 0 | 0 | 1 | 3 | 1 | 0 | 2 | 0 | 2 | 3 | 0 | 0 | 0 | 0 |
| VIII | 0 | 0 | 0 | 0 | 3 | 3 | 3 | 0 | 0 | 1 | 0 | 0 | 0 | 3 | 0 | 0 |
| IX | 0 | 0 | 0 | 0 | 0 | 2 | 0 | 0 | 0 | 0 | 3 | 0 | 0 | 0 | 0 | 0 |
| X | 0 | 0 | 0 | 0 | 2 | 3 | 2 | 0 | 1 | 3 | 3 | 3 | 0 | 2 | 1 | 0 |

It will be noticed that at one pound per acre the compounds of this invention are quite selective with respect to certain problem weeds. This property enables their use in planted fields where the particular susceptible weed is the principal problem.

When more general phytotoxicity is required the same compounds can be used at higher levels, for example at 5 pounds per acre. Table II shows the observed pre-emergent herbicidal effect at this higher level of application.

Table II

| Compound | A | B | C | D | E | F | G | H | I | J | K | L | M | N | O | P |
| --- | --- | --- | --- | --- | --- | --- | --- | --- | --- | --- | --- | --- | --- | --- | --- | --- |
| I | 1 | 1 | 1 | 0 | 2 | 3 | 2 | 0 | 3 | 2 | 3 | 3 | 0 | 2 | 2 | 0 |
| II | 3 | 3 | 3 | 3 | 3 | 3 | 3 | 3 | 3 | 3 | 3 | 3 | 3 | 3 | 3 | 3 |

Table II-continued

| Compound | Plant Species | | | | | | | | | | | | | | | |
|---|---|---|---|---|---|---|---|---|---|---|---|---|---|---|---|---|
| | A | B | C | D | E | F | G | H | I | J | K | L | M | N | O | P |
| III | 2 | 2 | 3 | 3 | 2 | 3 | 1 | 2 | 3 | 3 | 3 | 3 | 0 | 3 | 3 | 0 |
| IV | 3 | 3 | 3 | 3 | 3 | 3 | 2 | 2 | 3 | 3 | 3 | 3 | 1 | 3 | 3 | 2 |
| V | 3 | 3 | 3 | 3 | 3 | 3 | 0 | 1 | 3 | 2 | 3 | 3 | 1 | 3 | 3 | 0 |
| VI | 1 | 0 | 0 | 0 | 0 | 3 | 1 | 0 | 3 | 0 | 3 | 3 | 1 | 1 | 3 | 0 |
| VII | 3 | 1 | 1 | 0 | 2 | 3 | 1 | 0 | 3 | 0 | 3 | 3 | 1 | 2 | 1 | 0 |
| VIII | 3 | 2 | 3 | 3 | 3 | 3 | 2 | 1 | 3 | 3 | 3 | 3 | 2 | 3 | 3 | 1 |
| IX | 0 | 0 | 0 | 0 | 0 | 0 | 0 | 0 | 2 | 1 | 3 | 3 | 0 | 0 | 0 | 0 |
| X | 3 | 1 | 3 | 3 | 3 | 3 | 2 | 2 | 3 | 3 | 3 | 3 | 2 | 3 | 3 | 2 |

The phytotoxicity is also manifested by contact, for example spraying mature foliage to the saturation point (200 gallons per acre) with the solution at 0.2 percent (4 pounds per acre) or at 0.5 percent (10 pounds per acre) significant weed control was obtained. Table III describes contact activity of several of the subject compounds on a wide variety of plant genera:

Table III

| Compound | % Conc. | Plant Species | | | | | | | | | | | | | | | |
|---|---|---|---|---|---|---|---|---|---|---|---|---|---|---|---|---|---|
| | | A | B | C | D | E | F | G | H | I | J | K | L | M | N | O | P |
| II | 0.2 | 1 | 0 | 1 | 3 | 3 | 3 | 2 | 0 | 3 | 0 | 3 | 4 | 3 | 4 | 0 | 0 |
| V | 0.2 | 2 | 1 | 1 | 1 | 3 | 3 | 2 | 1 | 0 | 0 | 2 | 4 | 3 | 3 | 0 | 1 |
| VIII | 0.2 | 3 | 0 | 1 | 0 | 4 | 4 | 1 | 1 | 2 | 0 | 1 | 4 | 2 | 4 | 1 | 0 |
| VIII | 0.5 | 4 | 3 | 3 | 3 | 4 | 4 | — | — | 3 | — | 4 | 4 | 4 | 4 | 2 | — |

Other compounds and near homologues of the above described compounds having similar properties include for example:
2-methyl-4-(p-nitrophenyl)-3,5-dioxo-1,2,4-oxadiazolidine
2-methyl-4-phenyl-3,5-dioxo-1,2,4-oxadiazolidine
4-methyl-2-phenyl-3,5-dithiono-1,2,4-oxadiazolidine
4-ethyl-2-phenyl-3,5-dioxo-1,2,4-oxadiazolidine
2-(3',4'-dichlorophenyl)-3,5-dioxo-1,2,4-oxadiazolidine Pre-emergent activity can be observed at as low as 0.1 pounds per acre and under some circumstances as much as 10 pounds per acre is advantageous. The post-emergent use may also be applied at the rate of 0.1 to 10 pounds per acre. Where the foliage is well developed the saturation of plant surfaces may require the use of 2 to 10 pounds per acre. However, seedlings and very young plants can be effectively controlled with 0.1 to 2 pounds per acre.

The new phytotoxic compounds may be formulated in a variety of ways, for example as solids, liquids, emulsions and other dispersions.

The solid formulations, frequently referred to as "dusts" may contain in addition to the active ingredients, diluents or extenders, dispersing agents to prevent localized excessive concentrations, and agents to facilitate distribution in soil or soil waters. Suitable solid diluents are those which render the compositions permanently dry and free-flowing. Thus, hygroscopic materials are to be avoided, unless the compositions also contain a separate substance to serve as an aid to flowability. Solid diluents, preferably pulverulent or granular in form so as to be effective carriers for the active ingredient, are the natural clays, such as china clays and the attapulgites; other minerals in natural state, such as talc, pyrophyllite, quartz, diatomaceous earth, hydrous mica, fuller's earth, chalk, rock phosphate and sulfur; the chemically modified minerals, such as the acid washed bentonites, precipitated calcium phosphate, expanded vermiculite, precipitated calcium carbonate, colloidal silica; and activated charcoal, and the like. These diluents may represent a substantial portion, for example 40 to 98 percent by weight of the entire formulation as applied to plant or soil. The more concentrated toxicants may require dilution by the user in order to provide compositions for the most effective use. The concentrated solid phytotoxic formulations may be injurious to crop plants, but if they are mixed with the surface soil by means of a disk-plow or harrow at the time of application, this phytotoxicity can be minimized.

If the solid component is to be used as a carrier for the active ingredient there are some practical limitations on particle sizes. Obviously large particles (10 mesh) or greater should be avoided. Optimum practice requires a minimum of fines (smaller than 100 mesh). Preferred practice will utilize granular carriers of 15 to 60 mesh with a major portion between 20 and 50 mesh. A narrow range of particle sizes will facilitate distribution since both large particles and the fines interfere with the proper operation of the nozzles on the applicators. The mesh sizes are U.S. Standard screen sizes, the mesh size being the number of aperatures per inch.

The quantity of active component which can be adsorbed on the granules will to a great extent depend on the porosity of the mineral. The very porous vermiculite may carry much more than its own weight of active component, for example up to 75% of the composition. Clays which find extensive use may be formulated with 5 to 40% by weight of the toxicant, preferred usage ranging from 10% to 25%.

The described phytotoxic compounds may be formulated as wettable dusts by intimately mixing the carrier containing the active ingredients with surfactants, such as those described hereinafter. These are usually concentrated so that they may be mixed with a large excess of water to provide formulations of such concentration that they may be spread on soil or on undesired vegetation as required for effective control of undesired growth of plants.

A very useful formulation is the wettable powder which contains a portion of organic solvent, for example 2 to 20% to aid in the distribution by dissolving or dispersing the water-insoluble components. Suitable organic solvents for the active components are the alcohols, ketones, hydrocarbons, for example toluene, xylene, lauryl alcohol, ethylene dichloride, dioxane, acetone, methylethyl ketone, hexane, kerosene and chlorinated hydrocarbons or mixtures thereof. The proportions of such organic liquid additives depends upon the solubility properties of the active ingredient, and can be 1% or less or as much as 20% in order to provide a uniformly dispersible formulation which is capable of maintaining its dispersed state during storage, use and after application to the soil or plant surfaces.

A useful formulation of the phytotoxic compositions may be a solid or liquid concentrate of the active ingredient to which has been added formulation aids or conditioning agents so that the concentrates may be mixed with a suitable extender or diluent in the field at the time of use. Obviously, for this purpose mixtures of dispersing agents and active components will be prepared in advance with or without the addition of water. The solid or liquid formulations are preferably applied by mechanical equipment involving spraying or spreading the formulation on the soil, or on the plant surfaces being treated. For this purpose readily flowable compositions are required, in either liquid or solid state. Thus, a critical aspect of the invention is the fluent carrier without which the optimum herbicidal effects frequently cannot be achieved.

The phytotoxic compositions of this invention are preferably supplied to the plant growing medium in the form of emulsions or suspensions. Emulsions or suspensions are prepared by dispersing the phytotoxic component either per se or in the form of an organic solution thereof in water with the aid of a water-soluble surfactant. The term "surfactant" as employed here and in the appended claims is used as in Volume II of Schwartz, Perry and Berch's "Surface Active Agents and Detergents" (1958, Interscience Publishers, Inc., New York) in place of the expression "emulsifying agent", to connote generically the various "emulsifying agents", "dispersing agents", "wetting agents" and "spreading agents" that are adapted to be admixed with the active compounds of this invention in order to secure better wetting and spreading of the active ingredients in the water vehicle or carrier in which they are insoluble through lowering the surface tension of the water (see also Frear "Chemistry of Insecticides, Fungicides and Herbicides", second edition page 280). These surfactants include the well-known capillary active substances which may be anion-active (or anionic), cation-active (or cationic), or non-ionizing or (non-ionic) which are described in detail in Volume I and II of Schwartz, Perry and Berch's "Surface Active Agents and Detergents", (1958, Interscience Publishers, Inc., New York) and also in the November 1947 issue of Chemical Industries (pages 811–824) in an article entitled "Synthetic Detergents" by John W. McCutcheon and also in the July, August, September and October, 1952 issues of Soap and Sanitary Chemicals under the title "Synthetic Detergents". The disclosures of these articles with respect to surfactants, i.e. the anion-active, cation-active and non-ionizing capillary active substances are incorporated in this specification by reference in order to avoid unnecessary enlargement of this specification. The preferred surfactants are the water-soluble anionic surface-active agents and the water-soluble non-ionic surface active agents set forth in U.S. Pat. No. 2,846,398 (issued Aug. 5, 1958). In general it is preferred that a mixture of water-soluble anionic and water-soluble non-ionic surfactants be employed.

In all of the forms described above the dispersions can be provided ready for use in combatting noxious vegetation or they can be provided in a concentrated form suitable for mixing with or dispersing in other extending agents. As illustrative of a particularly useful concentrate is an intimate mixture of a oxadiazolidine of this invention with a water-soluble surfactant which lowers the surface tension of water in the weight proportions of 0.1 to 15 parts of surfactant with sufficent of the phytotoxicant of this invention to make 100 parts by weight. Such a concentrate is particularly adapted to be made into a spray for combatting various forms of noxious vegetation by the addition of water thereto. As illustrative of such a concentrate is an intimate mixture of 95 parts by weight of 2-methyl-4-(3',4'-dichlorophenyl)-3,5-dioxo-1,2,4-oxadiazolidine and 5 parts by weight of water-soluble non-ionic surfactant, such as the polyoxyethylene derivative of sorbitan monolaurate.

Another useful concentrate adapted to be made into a spray for combatting noxious vegetation is a solution (preferably as concentrated as possible) of an oxadiazolidine of this invention in an organic solvent therefor. The said liquid concentrate preferably contains dissolved therein a minor amount (e.g. 0.5 to 10 percent by weight of the weight of the novel phytotoxicant) of a surfactant (or emulsifying agent), which surfactant is also water-dispersible. As illustrative of such a concentrate is a solution of 4-methyl-2-phenyl-3,5-dioxo-1,2,4-oxadiazolidine in acetone which solution contains dissolved therein a water-soluble polyoxyethylene glycol non-ionic surfactant and a water-soluble alkylaryl sulfonate anionic surfactant.

Of the surfactants aforementioned in preparing the various emulsifiable, wettable or dispersible compositions or concentrates of this invention, the anionic and non-ionic surfactants are preferred. Of the anionic surfactants, the particularly preferred are the well-known water-soluble alkali metal alkylaryl sulfonates as exemplified by sodium decylbenzene sulfonate and sodium dodecylbenzene sulfonate. Of the non-ionic surfactants the particularly preferred are the water-soluble polyoxyethylene derivatives of alkylphenols (particularly isooctylphenol) and the water-soluble polyoxyethylene derivatives of the mono-higher fatty acid esters of sorbitan containing 15 to 30 moles of ethylene oxide per mole of sorbitan mono-ester of alkylphenol.

In all of the various dispersions described hereinbefore for phytotoxicant purposes, the active ingredient can be one or more of the compounds of this invention. The compounds of this invention can also be advantageously employed in combination with other toxicants, including, for example, nematocides, bactericides and insecticides. In this manner it is possible to obtain mixtures which are effective against a wide variety of pests and other forms of noxious life.

For example, phytotoxicants useful in combination with the above-described compounds include 2,4-dichlorophenoxyacetic acids, 2,4,5-trichlorophenoxyacetic acid, 2-methyl-4-chlorophenoxyacetic acid and the salts, esters and amides thereof; triazine derivatives, such as 2,4-bis(3-methoxypropylamino)-6-methylthio-S-triazine, 2-chloro-4-ethylamino-6-isopropylamino-S-triazine, and 2-ethylamino-4-isopropylamino-6-methylmercapto-S-triazine; urea derivatives, such as 3-(3,4-dichlorophenyl)-1,1-dimethyl urea and 3-(p-chlorophenyl)-1,1-dimethyl urea; acetanilides such as N-isopropyl-α-chloroacetanilide, N-ethyl-α-chloro-2-methylacetanilide and 2-tert-butyl-2'-chloro-6-methylacetanilide; and acetamides such as N,N-diallyl-α-chloroacetamide, N-(α-chloroacetyl)hexamethylene imine, and N,N-diethyl-α-bromoacetamide, and the like.

When operating in accordance with the present invention growth inhibiting amounts of the compound or a composition containing same are dispersed or distributed in any convenient fashion in soil or other growth media, for example by simple mixing with the soil or by applying to the surface of the soil and thereafter dragging or disking the soil to the desired depth, or by injection or drilling techniques whereby the phytotoxicant of this invention is deposited beneath the surface of the soil, or by employment of a liquid carrier (solvent or non-solvent) to accomplish the penetration and impregnation. The application of the spray and dust compositions to the surface of the soil may be accomplished by conventional methods, e.g. with power dusters, boom or hand sprayers or spray dusters.

While this invention has been described with respect to certain embodiments, it is to be understood that it is not so limited and that variations and modifications thereof obvious to those skilled in the art can be made without departing from the spirit and scope thereof.

The embodiments of the invention in which an exclusive property or privilege is claimed are defined as follows:

1. A method of controlling the growth of vegetation which comprises contacting said vegetation or the vegetation growth medium with a phytotoxic amount of a compound of the formula

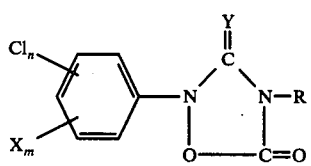

wherein X is alkyl of up to 4 carbon atoms, alkoxy of up to 4 carbon atoms or nitro, $n$ is an integer from zero to three, $m$ is zero or one, Y is oxygen or sulfur, and R is alkyl of up to 4 carbon atoms.

2. A method as defined in claim 1 wherein the vegetation is contacted with said compound.
3. A method as defined in claim 1 wherein the vegetation growth medium is contacted with said compound.
4. A method as defined in claim 2 wherein Y is oxygen and $m$ is zero.
5. A method as defined in claim 3 wherein Y is oxygen and $m$ is zero.
6. A method as defined in claim 4 wherein $n$ is one to three.
7. A method as defined in claim 5 wherein $n$ is one to three.
8. A method as defined in claim 6 wherein R is methyl.
9. A method as defined in claim 7 wherein R is methyl.
10. A method as defined in claim 1 wherein Y is oxygen, R is methyl, and $m$ and $n$ are each zero.
11. A method as defined in claim 1 wherein Y is sulfur, R is methyl, and $m$ and $n$ are each zero.
12. A method of destroying undesired vegetation which comprises applying to said vegetation a herbicidally effective amount of a compound of the formula

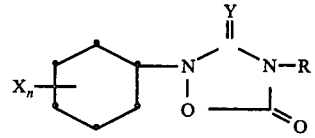

wherein R is lower alkyl, Y is a member of the group consisting of oxygen and sulfur, each X is independently selected from the group consisting of lower alkyl, lower alkoxy, nitro and halogen, and $n$ is an integer from 0 to 4, inclusive.

* * * * *